US009075009B2

(12) United States Patent
Kim et al.

(10) Patent No.: US 9,075,009 B2
(45) Date of Patent: Jul. 7, 2015

(54) SURFACE PLASMON RESONANCE SENSOR USING METALLIC GRAPHENE, PREPARING METHOD OF THE SAME, AND SURFACE PLASMON RESONANCE SENSOR SYSTEM

(75) Inventors: Taesung Kim, Suwon-si (KR); Byung Hee Hong, Seoul (KR); Jaeboong Choi, Yongin-si (KR); Atul Kulkarni, Suwon-si (KR); Hyeong Keun Kim, Hwaseong-si (KR)

(73) Assignee: SUNGKYUNKWAN UNIVERSITY FOUNDATION FOR CORPORATION COLLABORATION, Suwon-si (KR)

( * ) Notice: Subject to any disclaimer, the term of this patent is extended or adjusted under 35 U.S.C. 154(b) by 484 days.

(21) Appl. No.: 12/909,346

(22) Filed: Oct. 21, 2010

(65) Prior Publication Data
US 2011/0285999 A1    Nov. 24, 2011

(30) Foreign Application Priority Data

May 20, 2010 (KR) .......................... 10-2010-0047626

(51) Int. Cl.
*G01N 21/55* (2014.01)
*G01N 21/552* (2014.01)

(52) U.S. Cl.
CPC ............ *G01N 21/552* (2013.01); *G01N 21/554* (2013.01)

(58) Field of Classification Search
CPC . G01N 21/552; G01N 21/553; G01N 21/554; G01N 21/7703; G01N 21/648; G01N 2021/7713; G01N 2021/433; G01N 21/522; G01N 21/544; G01N 21/658; G02B 6/0229
USPC ......................................................... 356/445
See application file for complete search history.

(56) References Cited

U.S. PATENT DOCUMENTS

| 5,327,225 | A   | * | 7/1994  | Bender et al. ................. 356/445 |
| 5,359,681 | A   | * | 10/1994 | Jorgenson et al. .............. 385/12  |
| 5,822,073 | A   | * | 10/1998 | Yee et al. ...................... 356/445 |
| 7,456,972 | B2  | * | 11/2008 | Ke et al. ........................ 356/445 |
| 7,601,421 | B2  | * | 10/2009 | Khabashesku et al. .... 428/297.4 |
| 8,072,606 | B2  | * | 12/2011 | Chau et al. ..................... 356/445 |
| 8,139,617 | B2  | * | 3/2012  | Song ............................... 372/18 |
| 8,355,134 | B2  | * | 1/2013  | Chau et al. ..................... 356/445 |
| 2007/0153283 | A1 | * | 7/2007 | Tsao et al. ..................... 356/445 |
| 2010/0021708 | A1 | * | 1/2010 | Kong et al. .................... 428/220 |
| 2011/0048625 | A1 | * | 3/2011 | Caldwell et al. .............. 156/233 |
| 2012/0281209 | A1 | * | 11/2012 | Bai ............................... 356/301 |

OTHER PUBLICATIONS

Di et al., "Patterned Graphene as Source/Drain Electrodes for Bottom-Contact Organic Field-Effect Transistor", Advanced Materials, vol. 20, Issue 17, pp. 3289-3293, Sep. 3, 2008.*
Song, Y.W., et al., Single-walled carbon nanotubes for high-energy optical pulse formation, Applied Physics Letters 92, Jan. 16, 2008, pp. 3.*
Song et al. "Carbon nanotube mode lockers with enhanced nonlinearity via evanescent field interaction in D-shaped fibers" Optics Letters vol. 32, No. 2, Jan. 15, 2007.*
Maffucci et al. Graphene, Carbon Nanotubes, and Nanostructures Techniques and Applications, 2013.*

* cited by examiner

*Primary Examiner* — Michael A Lyons
*Assistant Examiner* — Shawn Decenzo
(74) *Attorney, Agent, or Firm* — NSIP Law (57) ABSTRACT

There is provided a surface plasmon resonance sensor including a metallic graphene layer formed in a core of a predetermined area of an optical fiber from which a jacket and a cladding are removed. Further, a preparing method of the surface plasmon resonance sensor and a surface plasmon resonance sensor system is also provided.

24 Claims, 12 Drawing Sheets

SURFACE PLASMON RESONANCE SENSOR USING METALLIC GRAPHENE, PREPARING METHOD OF THE SAME, AND SURFACE PLASMON RESONANCE SENSOR SYSTEM

CROSS-REFERENCE TO RELATED APPLICATION

This application claims the benefit of Korean Patent Application No. 10-2010-0047626 filed on May 20, 2010, the entire disclosures of which are incorporated herein by reference.

FIELD OF THE INVENTION

The present disclosure relates to a surface plasmon resonance sensor using a metallic carbon nanostructure layer such as a metallic graphene layer and a preparing method of the surface plasmon resonance sensor, and also relates to a surface plasmon resonance sensor system.

BACKGROUND OF THE INVENTION

Recently, a research on a surface plasmon resonance (SPR) sensor which has relatively high sensitivity (to about 1 pg/mm2) to an object to be detected and does not need a labeling process with a phosphorescent dye and by which a degree of a reaction can be monitored in real time has been carried out as a core technology in the fields of nano chemistry and biosensors.

A surface plasmon is a collective charge density oscillation occurring on a surface of a metallic thin film, and a surface plasmon wave (SPW) generated by the oscillation is a surface electromagnetic wave propagating along a boundary surface between metal and a dielectric material. If an external electric field is applied to an interface between two media having different dielectric functions, i.e., an interface between metal and a dielectric material, surface charges are induced at the an interface between the two media due to discontinuity of vertical components of the electric field and oscillation of the surface charges is represented as a surface plasmon wave.

An incident wave of a light emitted from a light source is reflected at the interface with the metallic thin film and an evanescent wave is exponentially decreased at the interface into the metallic thin film. At a specific incident angle and with a specific thickness of the metallic thin film, an incident wave parallel to a direction of the interface and a surface plasmon wave propagating along the interface between the metallic thin film and the dielectric material have the same phase, and a resonance thus occurs. In this case, all photoenergy of the incident wave is absorbed by the metallic thin film and a reflection wave thus disappears, which is referred to as a surface plasma resonance (SPR). Further, an angle of a minimum reflectivity of the incident light is referred to as a surface plasmon resonance angle.

As a structure or an environment of the dielectric material in contact with the surface of the metallic thin film is varied, an effective refractive index is varied and the resonance angle at which a surface plasmon resonance occurs, i.e., an angle of a minimum reflectivity, is thus varied. In this way, by using a principle of a surface plasmon resonance capable of optically measuring an environmental change in a material, it is possible to detect changes such as a selective binding or separation between various kinds of materials from a change in a resonance angle via an appropriate chemical or physical change on a surface layer of the metallic thin film.

A phenomenon of a surface plasmon resonance was first described in the early 1900s by Wood as a result of observation of anomalous diffraction due to excitation of surface plasma wave in Fano's metal diffraction lattice, and in 1968, Kretschmann and Otto demonstrated excitation of two surface plasmon resonances having different structures using prisms, showing general applicability of a surface plasmon resonance. Further, in 1970s, availability of a surface plasmon resonance for analyzing characteristics of a thin film and observing a change in a metallic interface was proved, and in 1982, Nylander and Liedberg used a surface plasmon resonance sensor for detecting a gas and as a bio sensor.

However, a conventional surface plasmon resonance (SPR) sensor has a problem of low sensitivity in analyzing a material of low concentration.

BRIEF SUMMARY OF THE INVENTION

In view of the foregoing, the present disclosure provides a surface plasmon resonance sensor including a metallic graphene layer, a preparing method of the surface plasmon resonance sensor, and a surface plasmon resonance sensor system including the surface plasmon resonance sensor.

However, the problem to be solved by the present disclosure is not limited to the aforementioned problem, and other problems can be clearly understood by those skilled in the art from the following description.

In accordance with one aspect of the present disclosure, there is provided a surface plasmon resonance sensor including a metallic graphene layer formed in a core of a predetermined area of an optical fiber from which a jacket and a cladding are removed.

In accordance with another aspect of the present disclosure, there is provided a preparing method of a surface plasmon resonance sensor. The preparing method includes exposing a core of a predetermined area of an optical fiber by removing a jacket and a cladding from the predetermined area of the optical fiber; and forming a metallic graphene layer in the exposed core of the optical fiber.

In accordance with still another aspect of the present disclosure, there is provided a surface plasmon resonance sensor system including a surface plasmon resonance sensor including a metallic graphene layer formed in a core of a predetermined area of an optical fiber from which a jacket and a cladding are removed; a light source unit that supplies an incident light to the metallic graphene layer; and a light receiving unit that senses a reflection light reflected by the metallic graphene layer among the incident light.

In accordance with the present disclosure, the surface plasmon resonance sensor including the metallic graphene layer has improved sensitivity and, thus, it is capable of easily detecting a minute amount of chemical materials or bio materials. Further, since the metallic graphene layer is formed on a wide range of the optical fiber, a separate polarization controller is not required. In particular, the metallic graphene layer has excellent metallic proeprty with high electronic conductivity and excellent mechanical strength and can be distributed in a large area. Therefore, by using such characteristics of the metallic graphene layer, the present disclosure provides a surface plasmon resonance sensor which has high mechanical strength and can be fabricated in a large area scale. In order to be operated at a fixed wavelength, the surface plasmon resonance sensor in accordance with the present disclosure does not need a buffer layer for shifting an effective refractive index of the SPW to a phase-matching condition because the sensor includes various cladding modes that can excite the SPW. That is, the excitation of the SPW is inherent in the plasmon resonance sensor.

BRIEF DESCRIPTION OF THE DRAWINGS

Non-limiting and non-exhaustive embodiments will be described in conjunction with the accompanying drawings. Understanding that these drawings depict only several embodiments in accordance with the disclosure and are, therefore not to be intended to limit its scope, the disclosure will be described with specificity and detail through the use of the accompanying drawings, in which.

DETAILED DESCRIPTION OF THE INVENTION

Hereinafter, embodiments and examples of the present invention will be described in detail with reference to the accompanying drawings in order for those skilled in the pertinent art to easily implement it.

However, it is to be noted that the present invention is not limited to the embodiments and the examples but can be implemented in various other ways. In the drawings, parts irrelevant to the description are omitted for the simplicity of explanation, and like reference numerals denote like parts through the whole document.

Through the whole document, the term "on" used to designate a position of one layer or element with respect to another layer or element includes both a case that one layer or element is "in contact with" another layer or element and a case that still another layer or element exists between two layers or elements. Moreover, the term "comprises or includes" and/or "comprising or including" used in the document means that one or more other components, steps, operation and/or existence or addition of elements are not excluded from the described components, steps, operation and/or elements but further included unless stated otherwise.

The terms "about or approximately" or "substantially" are intended to have meanings close to numerical values or ranges specified with an allowable error and intended to prevent accurate or absolute numerical values disclosed for understanding of the present invention from being illegally or unfairly used by any unconscionable third party.

The term "metallic graphene layer" used in the document refers to a layer or sheet of graphene which forms a polycylic aromatic molecule made of a multiple number of carbon atoms bonded by a covalent bond. The carbon atoms bonded by the covalent bond may form a 6-membered ring as a basic repeat unit but may further include 5-membered and/or 7-membered rings. Accordingly, the metallic graphene layer may exit as a monolayer of covalent-bonded (typically, $sp^2$-bonded) carbon atoms. The metallic graphene layer may have various structures, and their structures may depend on a 5-memberd and/or 7-membered ring content that may be included in the graphene. The metallic graphene layer may be a monolayer of graphene as mentioned above, but it may also be made of a plurality of graphene layers stacked together. Typically, the dangling bonds on the edge of the graphene may be saturated with a hydrogen atom.

In accordance with one aspect of the present disclosure, a surface plasmon resonance sensor includes a metallic graphene layer formed in a core of a predetermined area of an optical fiber from which a jacket and a cladding are removed.

Besides the metallic graphene layer, the surface plasmon resonance sensor may further include, but not limited thereto, metallic graphite, a metallic carbon nano tube (CNT) or the like.

In an illustrative embodiment, the core of the optical fiber may include at least one selected from a group consisting of an inorganic material, an organic material and a combination thereof but is not limited thereto. In the embodiment, the inorganic material may include at least one material selected from a group consisting of silica ($SiO_2$), aluminum oxide ($Al_2O_3$), hafnium oxide/hafnium silicate, and perovskite, but not limited thereto. In the embodiment, the organic material may include at least one material selected from a group consisting of a thermally curable aromatic resin, polydimethylsiloxane, polyvinylphenol (PVP), polyvinyliden fluoride (PVDF), polymethylmethacrylate (PMMA), polyethylene terephthalate (PET), polyethylene naphthalate (PEN), polycarbonate (PC), polyethylene, polypropylene, polystyrene, cyclic olefin copolymer (COC), polyacrylate (PAR), polyethersulfone (PES), polyimide (PI), and parylene, but not limited thereto.

In an exemplary embodiment, the optical fiber may include a multimode optical fiber but is not limited thereto.

In an exemplary embodiment, the core of the optical fiber on which the metallic graphene layer is formed may have a planar or curved surface shape but not limited thereto.

In an exemplary embodiment, the metallic graphene layer may include a monolayer of graphene or multilayers of graphene but is not limited thereto. By way of example, a thickness of the metallic graphene layer may be in the range from about 1 nm to about 1 μm but is not limited thereto.

In an exemplary embodiment, the surface plasmon resonance sensor may sense, but not limited to, a chemical material or a bio material.

In accordance with another aspect of the present disclosure, a preparing method of a surface plasmon resonance sensor may include exposing a core of a predetermined area of an optical fiber by removing a jacket and a cladding from the predetermined area of the optical fiber; and forming a metallic graphene layer in the exposed core of the optical fiber.

In an illustrative embodiment, the process of forming the metallic graphene layer in the exposed core of the optical fiber may include, but not limited to, floating the metallic graphene layer on a surface of distilled water and transferring the metallic graphene layer onto the exposed core of the optical fiber by bringing the floating metallic graphene layer into contact with the core area.

In an exemplary embodiment, the process of forming the metallic graphene layer in the exposed core of the optical fiber may include, but not limited to, transferring the metallic graphene layer onto a stamper, and transferring the metallic graphene layer onto the exposed core of the optical fiber by pressing the metallic graphene layer transferred on the stamper onto the exposed core of the optical fiber. In an exemplary embodiment, the metallic graphene layer may be coated on the core of the optical fiber by pressing the metallic graphene layer transferred on the stamper in a circumferential direction of the exposed core area, but not limited thereto.

In an exemplary embodiment, the process of forming the metallic graphene layer in the exposed core of the optical fiber may include, but not limited to, forming the metallic graphene layer on the exposed core of the optical fiber by a spraying method.

In an exemplary embodiment, the preparing method of the surface plasmon resonance sensor may further include treating a surface of the exposed core area of the optical fiber with UV or plasma, but not limited thereto.

In an exemplary embodiment, the metallic graphene layer may be made of a graphene film formed to have a controlled area and thickness by a chemical vapor deposition method, but not limited thereto.

In an exemplary embodiment, the preparing method of the surface plasmon resonance sensor may include forming a multilayered metallic graphene by repeating the process of forming the metallic graphene layer in the exposed core of the optical fiber, but not limited thereto.

In an exemplary embodiment, the preparing method of the surface plasmon resonance sensor may include all technical disclosures discussed above for the surface plasmon resonance sensor, and redundant description will be omitted for the simplicity of explanation.

In accordance with still another embodiment of the present disclosure, a surface plasmon resonance sensor system may include a surface plasmon resonance sensor including a metallic graphene layer formed in a core of a predetermined area of an optical fiber from which a jacket and a cladding are removed; a light source unit configured to supply incident light to the metallic graphene layer; and a light receiving unit configured to sense reflection light reflected by the metallic graphene layer among the incident light.

In an exemplary embodiment, the surface plasmon resonance sensor system may further include, but not limited to, a polarizer that P-polarizes the incident light or the reflection light.

In an exemplary embodiment, a light source of the light source unit may include any one of a TM- or P-polarized monochromatic light source, a white light source, a laser and a light emitting diode (LED), but not limited thereto.

In an exemplary embodiment, the light receiving unit may include, in its light receiving surface, any one of light receiving elements including a photodiode, a light amplifier, a photosensitive sheet, a CCD (Charge Coupled Device) image sensor and a CMOS (Complementary Metal-Oxide-Semiconductor) image sensor, but not limited thereto.

In an exemplary embodiment, the surface plasmon resonance sensor may sense, but not limited to, a chemical material or a bio material.

In an exemplary embodiment, the metallic graphene layer may be a monolayer or a multilayer but is not limited thereto.

In an exemplary embodiment, the surface plasmon resonance sensor system may include all technical disclosures discussed above for the surface plasmon resonance sensor and the preparing method thereof, and redundant description will be omitted for the simplicity of explanation.

Hereinafter, a surface plasmon resonance sensor, a preparing method of the same, and a surface plasmon resonance sensor system in accordance with an embodiment of the present disclosure will be explained in detail with reference to the accompanying drawings. However, the present disclosure is not limited thereto.

Figure 1:
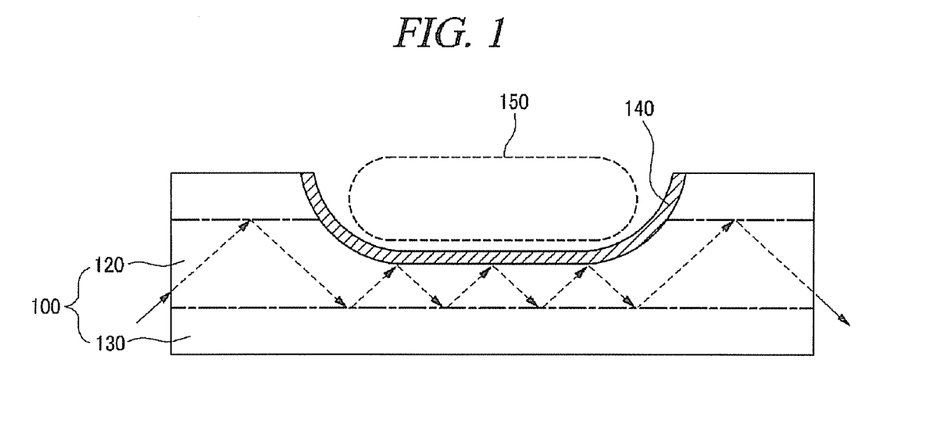
FIG. 1 is a cross sectional view of a surface plasmon resonance sensor including a metallic graphene layer in accordance with an embodiment of the present disclosure.

FIG. 1 is a cross sectional view of a surface plasmon resonance sensor in accordance with an embodiment of the present disclosure. The surface plasmon resonance sensor may include a metallic graphene layer 140 formed in a core 120 of a predetermined area of an optical fiber 100 from which a jacket (not shown) and a cladding 130 are removed.

Light supplied from a light source unit is incident to the core 120 of the optical fiber at a fixed angle and reaches a sensing part having the metallic graphene layer formed in the core of the predetermined area of the optical fiber while being totally reflected within the core. When a parallel wave vector component incident to the metallic graphene layer 140 of the sensing part coincides with a wave vector of the surface plasmon, most of the energy of the incident light may be absorbed into the metallic graphene layer. This phenomenon is called a surface plasmon resonance phenomenon. Conditions for resonance absorption of the surface plasmon may vary sensitively depending on an existence, a thickness or a mass of a sensing target material 150 and, also, depending on a concentration of the sensing target material 150 if the sensing target material 150 is a liquid. Since such a variation may cause a change in a reflectivity and/or an effective refractive index of light, a change in the refractive index, the mass, the thickness or the concentration of the sensing target material can be calculated quantitatively by measuring a resonance angle or a resonance wavelength at which the reflection light is minimized or by measuring a variation of the reflectivity through the light receiving unit 30. The sensing target material may be a chemical material or a bio material, but not limited thereto. As stated above, unlike in a conventional method of preparing a surface plasmon resonance sensor by using a metal, the present disclosure provides the surface plasmon resonance sensor including the metallic graphene layer.

Figure 2:
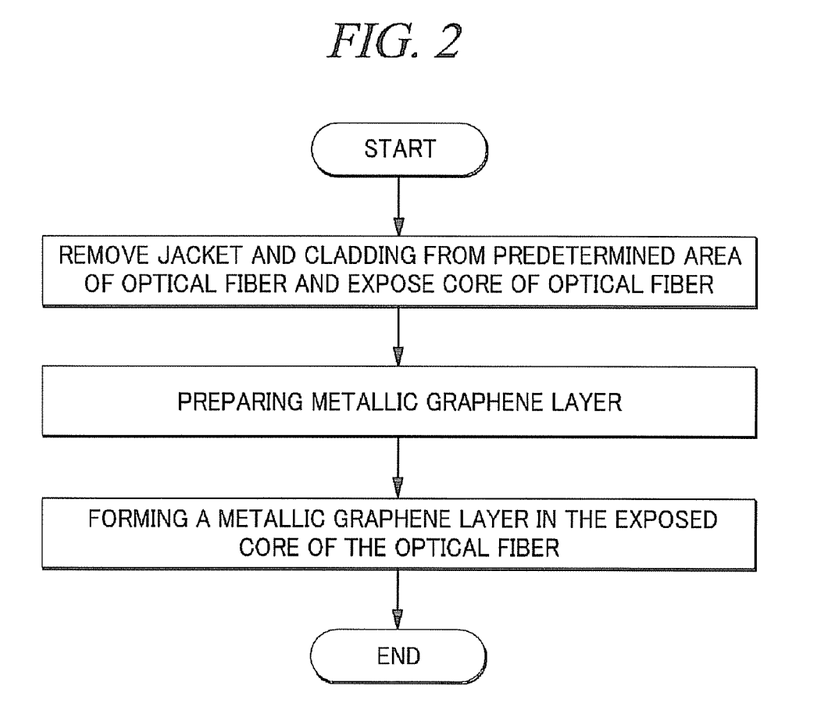
FIG. 2 is a flowchart for describing a method for preparing the surface plasmon resonance sensor including the metallic graphene layer in accordance with one embodiment of the present disclosure.
Figure 3:
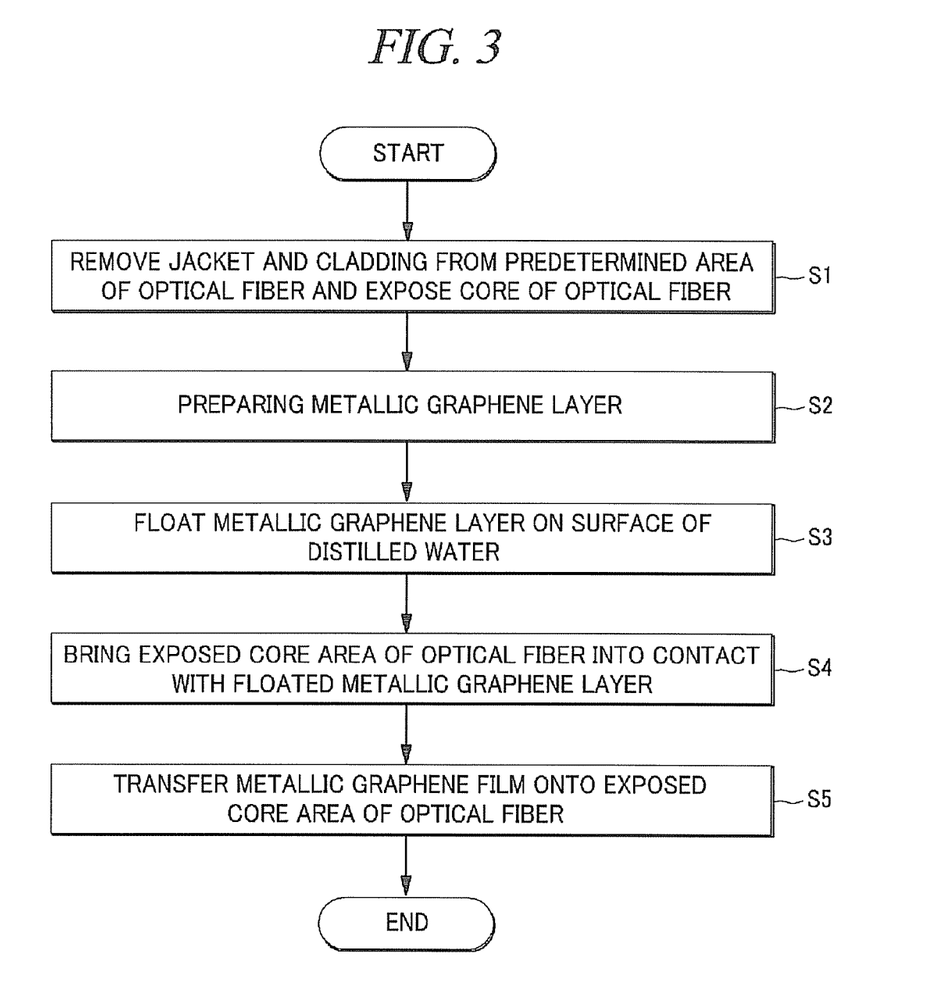
FIG. 3 is a flowchart for describing a method for preparing the surface plasmon resonance sensor including the metallic graphene layer in accordance with another embodiment of the present disclosure.

FIGS. 2, 3 and 4 are a flowchart and a process diagram for describing a method for preparing a surface plasmon resonance sensor including a metallic graphene layer formed in a core of a predetermined area of an optical fiber from which a jacket and a cladding are removed.

A preparing method of a surface plasmon resonance sensor in accordance with an embodiment of the present disclosure may include exposing a core of an optical fiber by removing a jacket and a cladding on a predetermined area of the optical fiber (step S1), preparing a metallic graphene layer (step S2), floating the metallic graphene layer on a surface of distilled water (step S3), bringing the floating metallic graphene layer into contact with the exposed core area of the optical fiber (step S4) and transferring the metallic graphene layer onto the exposed core area of the optical fiber by the contact (step S5).

Figure 4A:
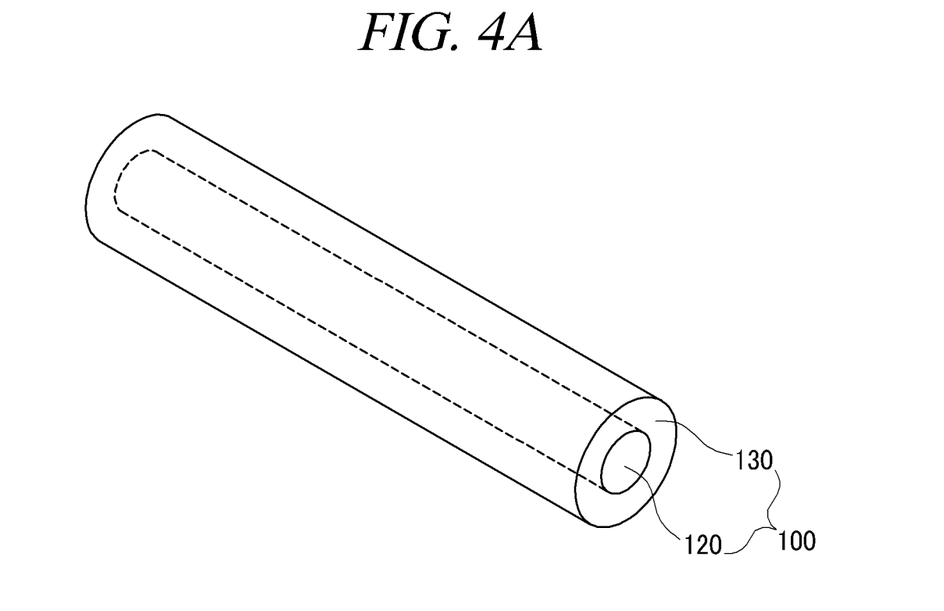
FIGS. 4A-4I are process diagrams for describing the method for preparing the surface plasmon resonance sensor including the metallic graphene layer in accordance with an embodiment of the present disclosure.
Figure 4B:
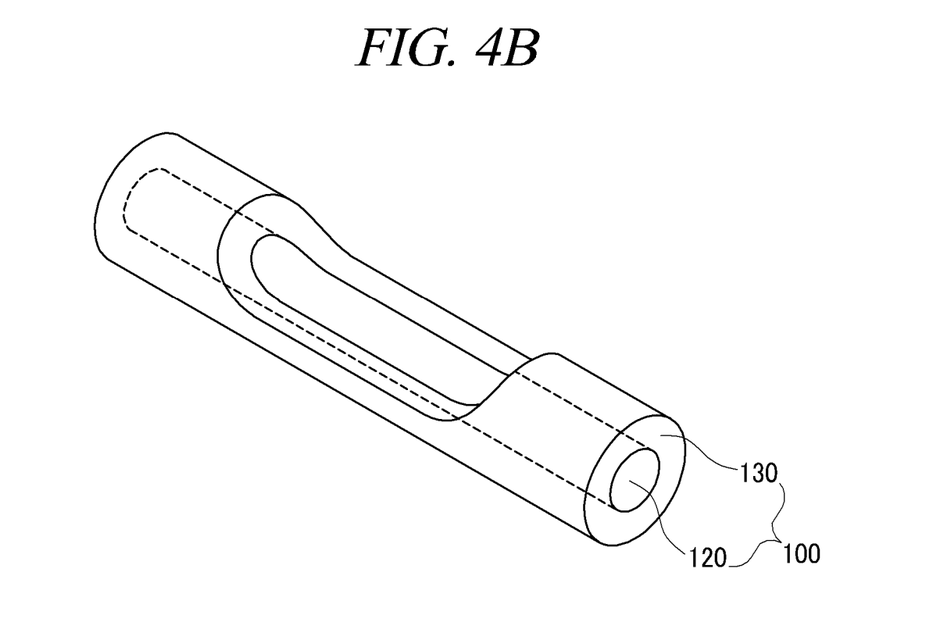

To elaborate, a jacket and a cladding are removed from a predetermined area of an optical fiber, and, thus, a core of the optical fiber is exposed (step S1). If the jacket (not illustrated) is removed by a device for stripping coating from the optical fiber 100, only the core 120 and the cladding 130 may be left (FIG. 4A, FIG. 4B). Then, both ends of the optical fiber can be planarized with a sheet of fine sandpaper. Here, this planarization process is very important for connection between the optical fiber and the light receiving unit. Generally, in the planarization process, the optical fiber may be rotated on the sheet of sandpaper until a desired planarization rate is obtained. Thereafter, the cladding 130 is removed. The cladding of the optical fiber can be removed by using a solvent such as N,N-dimethylformamide. A chemical-treated clean cloth may be soaked in the solvent, and the cladding of the optical fiber may be removed by being rubbed with the cloth. Since the cladding is weakened by the chemical solvent, if the optical fiber is put in the clean cloth and then is pulled back, only the cladding may be removed while the core is exposed. Here, when removing the jacket (not illustrated) and the cladding, attention should be paid so as not to cause damage on the core.

The exposed core area may serve as a sensing part for detecting a chemical or bio material to be detected. The exposed core area can be cleaned with secondary distilled water and a nitrogen gas. Then, the optical fiber is stored in a vacuum chamber so as to prevent contamination of the exposed core of the optical fiber. Additionally, before coating the metallic graphene layer on the exposed core of the optical fiber, a UV/ozone treatment (or a plasma surface treatment) may be performed on the surface of the exposed core of the optical fiber as a pre-treatment.

Subsequently, a metallic graphene layer 140 is prepared (step S2), and the prepared metallic graphene layer 140 is transferred onto the core of predetermined area of the optical fiber from which the jacket and the cladding are removed in the step S1 (steps S2, S3, S4 and S5).

In accordance with the embodiment of the present disclosure, the process of preparing the metallic graphene layer will be explained in further detail with reference to FIG. 4.

Figure 4C:
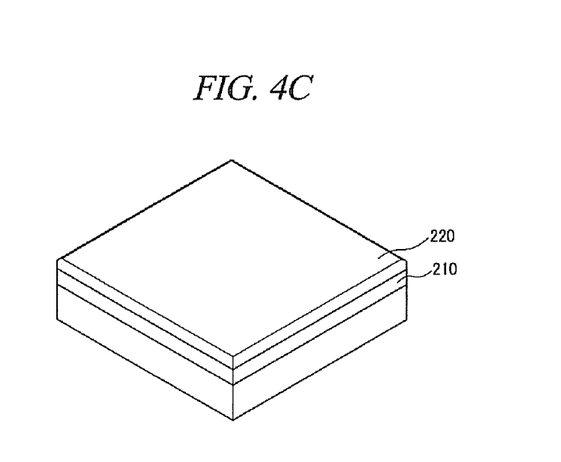

A metallic catalyst thin film for graphene growth 220 is formed by depositing a metal on a substrate 210 in the form of a thin film by using a thermal evaporator, an e-beam evaporator or a sputter or by using an electroplating method or the like (FIG. 4C). The metallic catalyst thin film for graphene growth 220 may include at least one metal or alloy selected from a group consisting of Ni, Co, Fe, Pt, Au, Al, Cr, Cu, Mg, Mn, Rh, Si, Ta, Ti, W, U, V, Zr, brass, bronze, stainless steel, and Ge, but not limited thereto. The substrate 210 may include various metallic foil/sheets made of nickel, stainless steel, and copper as well as a substrate made of silicon oxide/silicon. Further, the substrate and the metallic catalyst thin film for graphene growth may have patterns. In the embodiment, the metallic catalyst thin film for graphene growth may have a thickness equal to or larger than about 10 nm. By way of example, the thickness of the metallic catalyst thin film for graphene growth may range from about 10 nm to about 100 μm, from about 10 nm to about 10 μm, from about 10 nm to about 1 μm, from about 10 nm to about 500 nm, from about 10 nm to about 300 μm, from about 100 nm to about 100 μm, from about 100 nm to about 10 μm, from about 100 nm to about 1 μm, from about 100 nm to about 500 nm, or from about 100 nm to about 300 nm, but not limited thereto.

Then, a metallic graphene is grown on the substrate including the metallic catalyst thin film for graphene growth. In the embodiment, the graphene can be grown by supplying a carbon source and heat to the substrate including the metallic catalyst thin film for graphene growth. By way of example, if the substrate is heat-treated at a temperature of about 300° C. to about 2000° C. while supplying a carbon source such as carbon monoxide, carbon dioxide, methane, ethane, ethylene, ethanol, acetylene, propane, butadiene, pentane, pentene, cyclopentadiene, hexane, cyclohexane, benzene, or toluene in a gas phase, carbon components present in the carbon source may be bonded to each other to form a hexagonal plate-shaped structure, resulting in that graphene can be grown.

The method of growing the metallic graphene may be implemented in various ways as long as a chemical vapor deposition method typically employed in the pertinent art is used. By way of example, the chemical vapor deposition method may include, but not limited to, rapid thermal chemical vapor deposition (RTCVD), inductively coupled plasma-chemical vapor deposition (ICP-CVD), low pressure chemical vapor Deposition (LPCVD), atmospheric pressure chemical vapor deposition (APCVD), metal organic chemical vapor deposition (MOCVD) or plasma-enhanced chemical vapor deposition (PECVD). By the above-mentioned method, metallic graphene of a large area having a horizontal or vertical length ranging from, e.g., about 1 mm to about 1000 m can be prepared, and, further, metallic graphene of a large area by the above-mentioned method have a uniform structure and few defects. Further, the metallic graphene may include a monolayer or a multilayer of graphene.

Figure 4D:
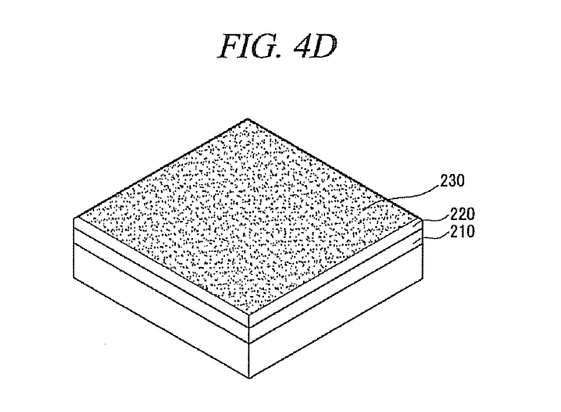

In the embodiment, the substrate including the metallic catalyst thin film for graphene growth is introduced into a thermal chemical vapor depositing chamber and is heated to about 1000° C. under an argon gas atmosphere. By heating the substrate including the metallic catalyst thin film for graphene growth in the reaction chamber while a supplying hydrogen gas thereto, an oxide layer and impurities on the metallic catalyst thin film for graphene growth can be removed. Further by reducing the catalyst layer by the hydrogen gas, an optimum catalyst layer condition for forming wide grain may be obtained. Thereafter, while heating the metallic catalyst thin film for graphene growth at a high temperature, a carbon containing gas is supplied into the reaction chamber together with an argon (Ar) gas or a helium (He) to thereby form a carbon layer 230 as shown in FIG. 4D.

Figure 4E:
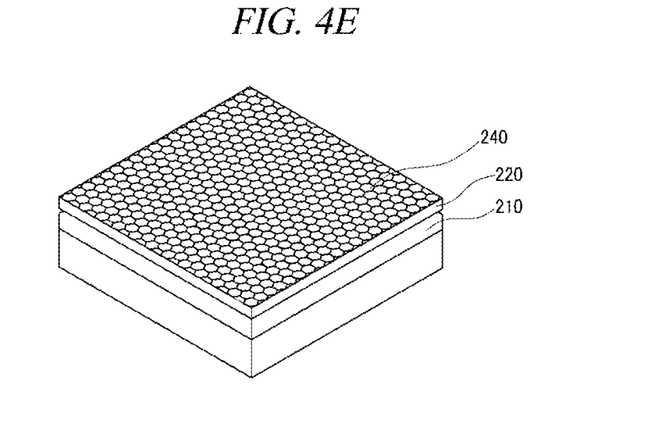

In case of using a plasma-enhanced chemical vapor deposition (PECVD) method generating plasma by applying an electric field after a vacuum level is increased, a growth temperature can be lowered. If cooling is performed rapidly after enough carbon is adsorbed into the metallic thin film, carbon may be separated from the metallic catalyst thin film for graphene growth 220 such as a nickel (Ni) layer and may be crystallized on a surface of the metallic catalyst thin film for graphene growth 220. As a result, it is possible to form a metallic graphene layer having various numbers of layers therein depending on the amount of the carbon. Further, by optimizing a cooling temperature while using argon, cooling condition allowing few detects and capable of minimizing amorphous carbon can be obtained, so that formation of the graphene layer 240 can be successfully completed (FIG. 4E).

The thickness of the metallic graphene layer 140 formed as discussed above can be controlled by adjusting a thickness of the metallic catalyst thin film for graphene growth, a reaction time, or a cooling rate. By way of example, as the reaction time and the thickness of the metallic catalyst thin film decrease, a thinner graphene layer can be formed. Further, the thickness of the formed metallic graphene layer can be controlled again by irradiating UV having an intensity of about several tens of W at normal temperature and pressure.

Figure 4F:
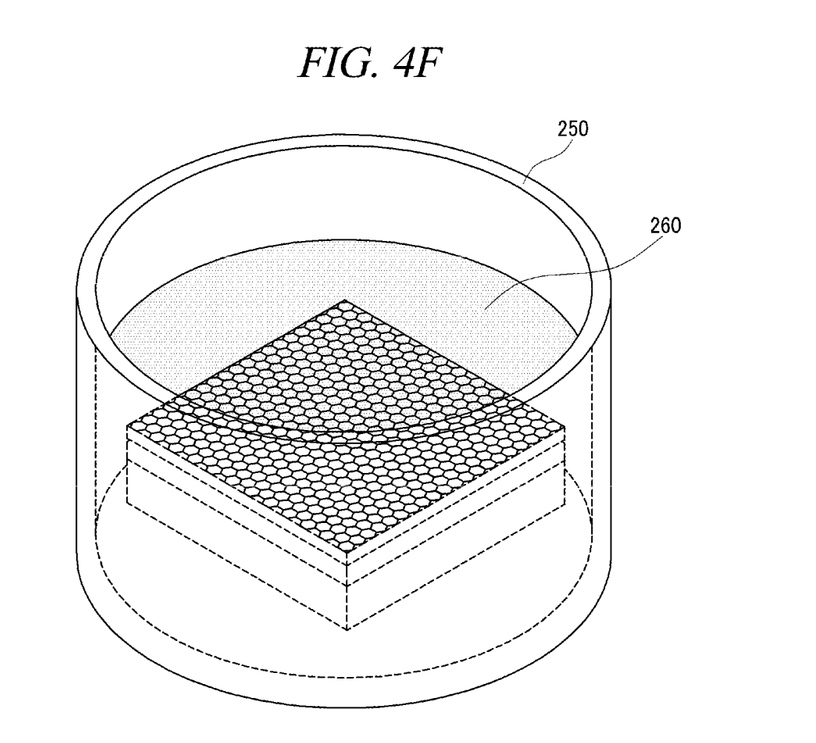
Figure 4G:
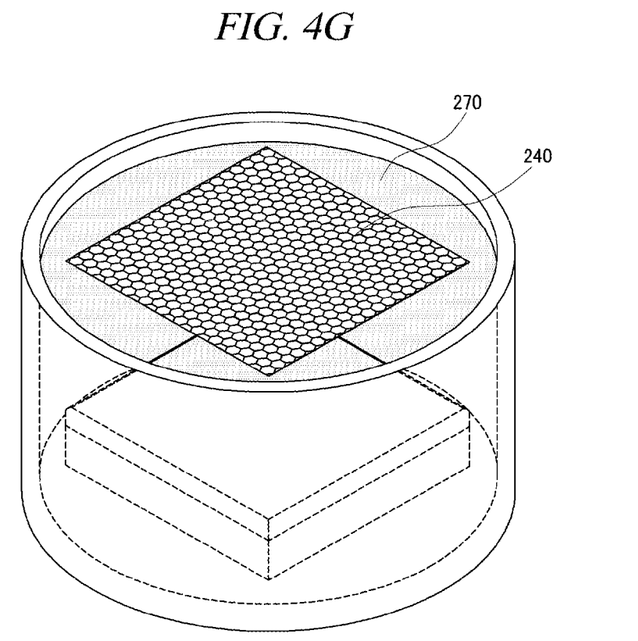

The metallic graphene layer can be separated from the substrate by removing the metallic catalyst thin film for graphene growth on the substrate using various acid solutions 260 in tank 250 as shown in FIG. 4F including an acid such as HF, BOE, $FeCl_3$, or $Fe(NO_3)_3$ and can be transferred to various substrates. By way of example, the various substrates may be an optical fiber of which core is exposed by removing a jacket and a cladding from a predetermined area thereof.

In the embodiment, an aqueous solution (1 M) of iron chloride (III) ($FeCl_3$) for removing the metallic catalyst thin film for graphene growth may be used as an oxide etchant, and, by way of example, a net ionic equation of such an etching reaction may be expressed as follows in case that the metallic catalyst thin film for graphene growth includes Ni:

$2Fe^{3+}(aq)+Ni(s) \rightarrow 2Fe^{2+}(aq)+Ni^{2+}(aq)$.

In such an oxidation/reduction process, the nickel thin film can be gradually and effectively etched in a neutral pH range without generating a gas by-product or a deposit. After a lapse of several minutes, the metallic graphene layer may be floated on the acid solution as can be seen from FIG. 4G, which means that the metallic graphene layer is ready to be transferred to the sensing part of the optical fiber. Thereafter, the metallic graphene layer can be sufficiently cleaned with distilled water (DIW) 270 four times or more and can be immersed in the distilled water (DIW) 270.

Figure 4H:
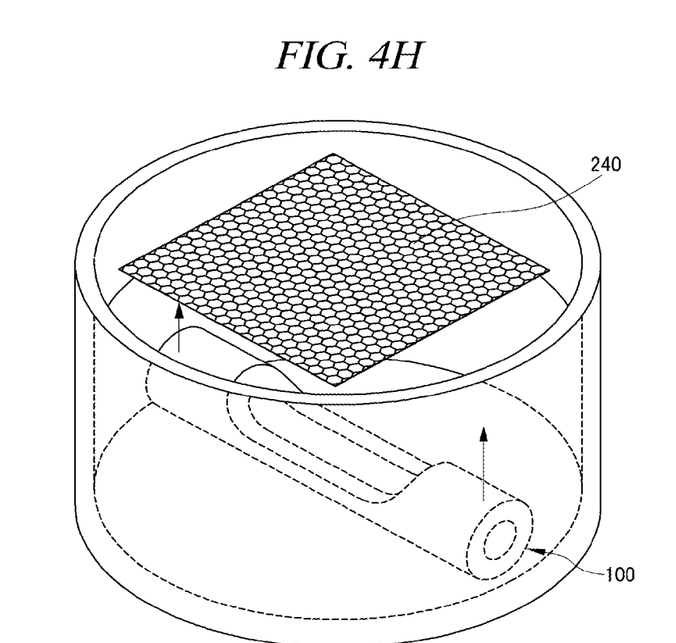
Figure 4I:
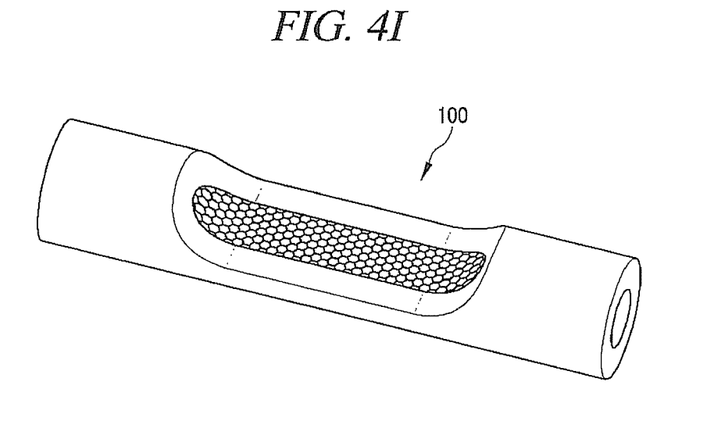

Referring to FIG. 4H, the optical fiber of which core is exposed by removing the jacket and the cladding from the predetermined area thereof is then put into a vessel, and the sensing part including the exposed core area of the optical fiber 100 as shown in FIG. 4I and the metallic graphene layer are aligned to each other. Then, the metallic graphene layer can be coated on or jointed to the sensing part by a deep coating method. Thereafter, a UV/ozone treatment (or a plasma surface treatment) may be performed on the surface of the sensing part coated or joined with the metallic graphene layer as an after-treatment.

Figure 5:
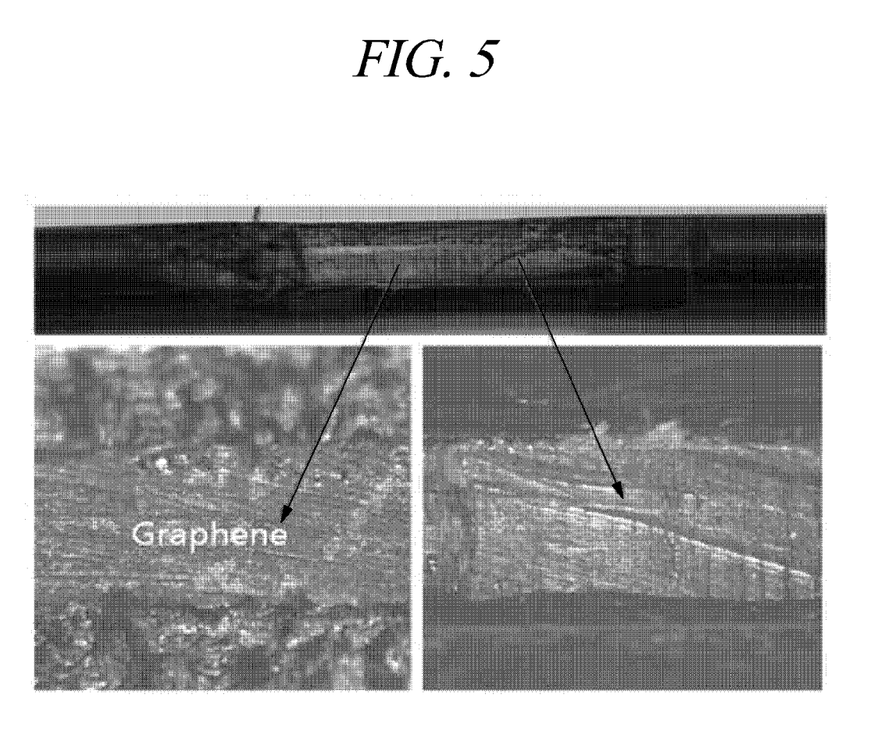
FIG. 5 is a photograph of a surface plasmon resonance sensor including a metallic graphene layer in accordance with an example of the present disclosure.

In another embodiment for forming the metallic graphene layer on the sensing part of the surface plasmon sensor, the metallic graphene layer may be joined to the sensing part by using a stamper (not shown). To elaborate, the metallic graphene layer obtained as can be seen from FIG. 4E may be transcribed onto the stamper made of an elastomer such as PDMS. Then, a protective film which can be freely bent and stretched and includes an elastomer having porous nano holes may be formed on the metallic graphene layer by a photolithography process. Thereafter, the stamper is aligned to the optical fiber of which core at the predetermined area is exposed by removing the jacket and the cladding, and the stamper is pressed onto the optical fiber having the exposed core. Then, by separating the stamper and the metallic graphene film from each other, the metallic graphene layer can be transferred onto the optical fiber having the exposed core. Then, the optical fiber coated with the metallic graphene layer may be cleaned and dried. By performing such a drying process at, e.g., about 70° C. for about 30 minutes or longer, adhesivity of the metallic graphene layer can be improved. In this way, the optical fiber including the metallic graphene layer 140 formed on the predetermined core area of the optical fiber can be prepared. FIG. 5 is a scanning electron micrograph of the surface plasmon resonance sensor including the metallic graphene layer prepared in accordance with the above-described embodiment of the present disclosure.

In still another embodiment for forming the metallic graphene layer on the sensing part of the surface plasmon sensor, the metallic graphene layer may be formed on one surface of the exposed optical fiber by spraying method. Such a spraying method may include dispersing the metallic graphene in an appropriate solvent and dispersing it in a prism. The solvent may be of any kind as long as the metallic graphene can be dispersed therein. By way of example, the solvent may be, but not limited to, water or an organic solvent such as alcohol.

Figure 6:
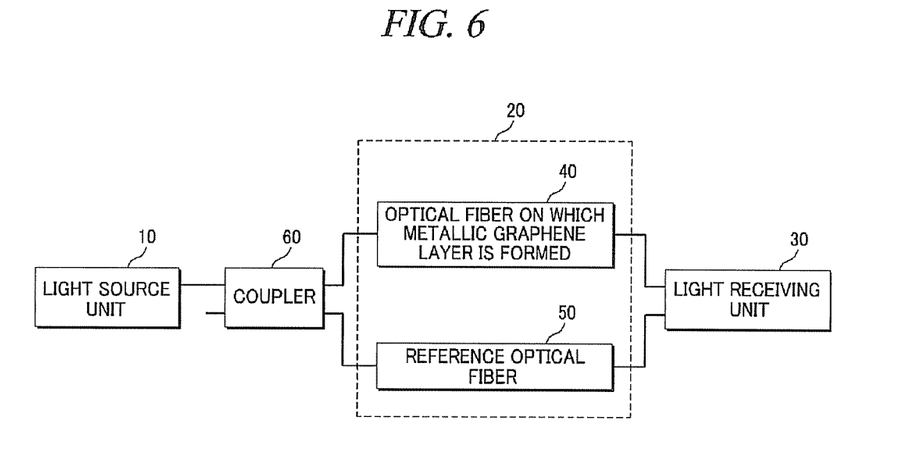
FIG. 6 is a schematic configuration view of a surface plasmon resonance sensor system in accordance with an embodiment of the present disclosure.

A plasmon resonance sensor system in accordance with the present disclosure may include a surface plasmon resonance sensor 40 including a metallic graphene layer formed in a core of a predetermined area of an optical fiber from which a jacket and a cladding are removed; a light source unit 10 configured to supply incident light to the metallic graphene layer; and a light receiving unit 30 configured to sense reflection light reflected by the metallic graphene layer among the incident light. Referring to FIG. 6, the surface plasmon resonance sensor system in accordance with an embodiment of the present disclosure may further include a coupler 60 and/or a reference optical fiber 50.

A light source provided by the light source unit 10 may cause a surface plasmon resonance phenomenon on the metallic graphene layer, and the light source may include any one of a TM- or P-polarized monochromatic light source, a white light source, a laser and a light emitting diode (LED), but not limited thereto. The light source may have wavelengths of UV to visible light (200 nm to 800 nm), but is not limited thereto.

In the surface plasmon resonance sensor 40 including the metallic graphene layer, reflectivity varies due to the aforementioned surface plasmon resonance phenomenon if a sensing target material such as a chemical or a bio material exists. The surface plasmon resonance sensor in accordance with the present disclosure is designed to use a surface plasmon phenomenon occurring in the graphene layer having metallic property instead of using a metal, unlike in a conventional sensor using a surface plasmon phenomenon occurring at an interface between a dielectric layer and the metal.

A chemical material or a bio material tends to be more easily adhered to the surface of the metallic graphene layer than to the surface of the metal. Besides, since the metallic graphene layer itself has highly advantageous optical property, sensitivity of the surface plasmon resonance sensor using the metallic graphene layer can be improved. Furthermore, in case that the metallic graphene layer is multilayered, the surface plasmon resonance phenomenon may occur in each of metallic graphene layers, intensity of reflectivity and effective refractive index may be increased. Therefore, even a minute amount of chemical material or bio material can be easily detected.

Meanwhile, since the reference optical fiber 50 has no metallic graphene layer, reflectivity is maintained constant regardless of presence of a chemical material or a bio material. The light receiving unit measures a variation of reflectivity of light passing through the sensing part having two optical fibers and can detect presence of the chemical material or the bio material as a sensing target material.

The light receiving unit 30 collects light reflected from the optical fibers and may include a photodiode, a light amplifier, a photosensitive sheet, and an image sensor such as a CCD or a CMOS, not limited thereto.

The coupler 60 may supply a light source from the light source unit 10 by splitting it in two directions toward the optical fiber including the metallic graphene layer and toward the reference optical fiber.

In accordance with some embodiments of the present disclosure, the optical-fiber SPR sensor based on a multilayer (typically less than 10 nm) of graphene films, which is deposited uniformly on the modified core of an optical fiber, show a localized surface plasmon (LSP) excitation in the UV/Visible range (200 to 800 nm). This sensor simply employs core mode to the co-propagating graphene cladding mode that can excite a SPW and monitors the change of the transmitted core mode power at a fixed wavelength to sense the variation of the refractive index of analyte. In other words, changes in the dielectric properties of the contacting medium influence the excitation of surface plasmons and hence the LSP absorption band, providing a scheme for optical sensing in the transmission and reflection surface plasmon resonance mode.

Figure 7:
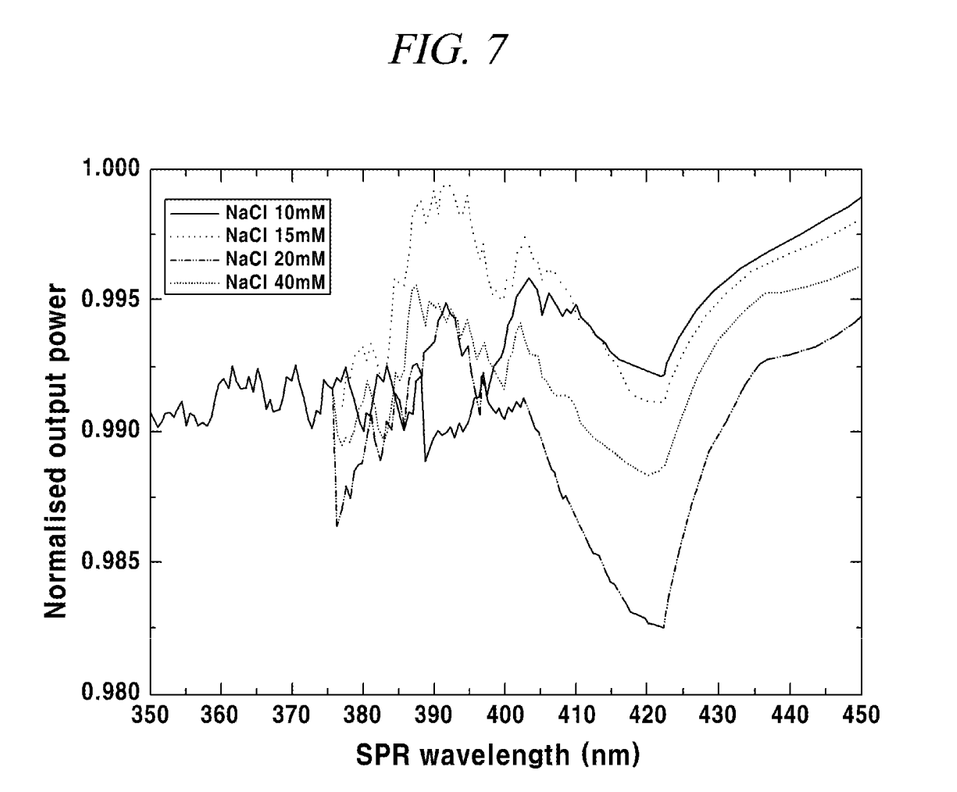
FIG. 7 is a graph showing a result of sensing a chemical material by using the surface plasmon resonance sensor in accordance with an example of the present disclosure.
Figure 8:
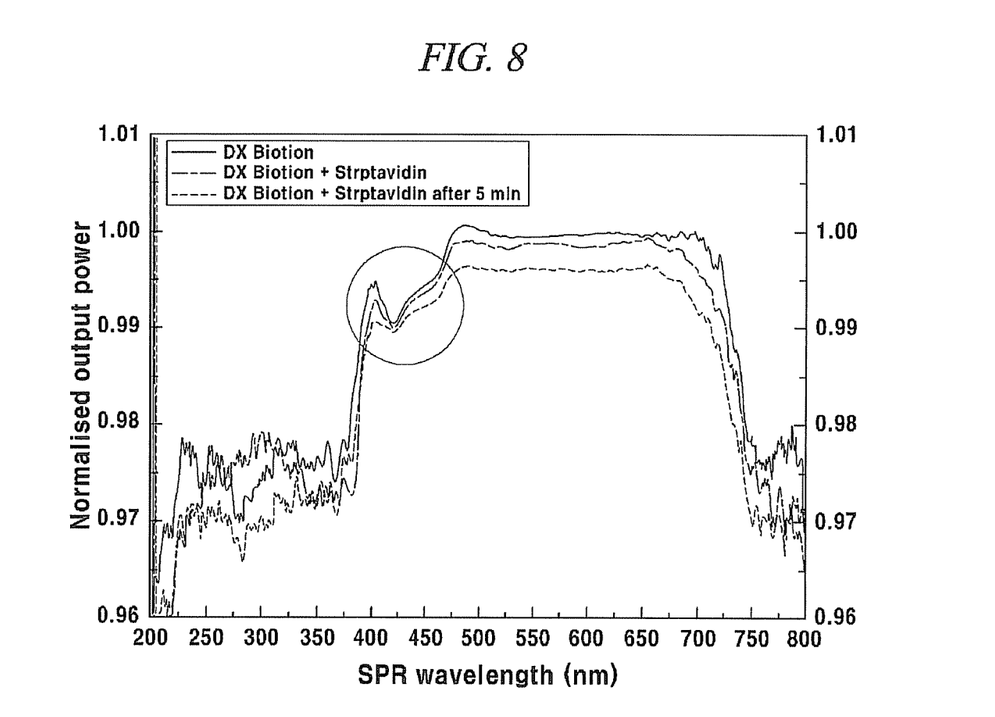
FIG. 8 is a graph showing a result of sensing a bio material by using the surface plasmon resonance sensor in accordance with an example of the present disclosure.

FIG. 7 and FIG. 8 show results of sensing NaCl as a chemical material and DX biotin as a biomaterial by using the surface Plasmon resonance sensor in accordance with an example of the present disclosure, respectively.

Referring to FIG. 7, changes in the transmittance intensity of the surface plasmon resonance sensor were monitored by using NaCl aqueous solution of various NaCl concentrations. It can be seen that the shift of the local surface plasmon resonance (LSPR) band positions took place near resonance wavelength range of 400 nm to 450 nm and the transmission peak intensities were gradually reduced with increasing the concentration of NaCl solutions.

Referring to FIG. 8, changes in the transmittance intensity of the surface plasmon resonance sensor were monitored for "DX Biotin" DNA nanostructure with immobilization of "Streptavidin" protein. It can be seen that the transmittance intensity were reduced after interaction of the DX Biotin DNA nanostructures with the Streptavidin protein. Also transmittance intensity change was observed as a function of DNA nanostructure and protein immobilization time after 5 minutes. It can also be seen that the transmission peak intensities were reduced at the resonance wavelength range of about 400 to 450 nm.

In accordance with some embodiments of the present disclosure, the graphene-coated fiber optic surface plasmon resonance spectroscopy was shown to be applicable to both chemically and physically adsorbed molecules, in liquid or gas phase, with measurements carried out either ex-situ or in-situ (real-time measurements).

The graphene-coated fiber optic surface plasmon resonance sensor in accordance with some embodiments of the present disclosure is low cost, easy to implement as there is no need to use or deposit controlled nano-metric range Au or Ag film/nanoparticles.

The present disclosure described above is not limited to the foregoing embodiments, examples and the accompanying drawings, and it would be understood by those skilled in the art that various changes and modifications may be made without changing technical conception and essential features described in the claims of the present invention.

What is claimed is:

1. A surface plasmon resonance sensor comprising:
   a metallic graphene layer formed in a core of a predetermined area of an optical fiber from which a jacket, and a cladding and a portion of the core are removed
   wherein the metallic graphene layer is a planar monolayer sheet of graphene or a plurality of planar monolayer sheets of graphene stacked together.

2. The surface plasmon resonance sensor of claim 1, wherein the core of the optical fiber includes at least one selected from a group consisting of an inorganic material, an organic material and a combination thereof.

3. The surface plasmon resonance sensor of claim 1, wherein the optical fiber includes a multimode optical fiber.

4. The surface plasmon resonance sensor of claim 1, wherein the core of the optical fiber on which the metallic graphene layer is formed has a planar or curved surface shape.

5. The surface plasmon resonance sensor of claim 1, wherein the metallic graphene layer is single-layered or multi-layered.

6. The surface plasmon resonance sensor of claim 1, wherein the surface plasmon resonance sensor senses a chemical material or a bio material.

7. The surface plasmon resonance sensor of claim 1, wherein the metallic graphene layer is formed in the core on a depression provided in the core of the predetermined area of the optical fiber.

8. The surface plasmon resonance sensor of claim 1, wherein a ring structure of the metallic graphene layer is formed substantially parallel to the metallic graphene layer formed in the core, wherein the ring structure is a 5-membered, 6-membered, or 7-membered ring structure.

9. A preparing method of a surface plasmon resonance sensor, the method comprising:
   exposing a core of a predetermined area of an optical fiber by removing a jacket, and a cladding and a portion of the core from the predetermined area of the optical fiber; and
   forming a metallic graphene layer in the exposed core of the optical fiber
   wherein the metallic graphene layer is a planar monolayer sheet of graphene or a plurality of planar monolayer sheets of graphene stacked together.

10. The preparing method of claim 9, wherein the process of forming the metallic graphene layer in the exposed core of the optical fiber includes:
    floating a metallic graphene layer on a surface of distilled water; and
    transferring the metallic graphene layer in the exposed core of the optical fiber by bringing the floating metallic graphene layer into contact with the exposed core of the optical fiber.

11. The preparing method of claim 9, wherein the process of forming the metallic graphene layer in the exposed core of the optical fiber includes:
    transferring a metallic graphene layer onto a stamper; and
    transferring the metallic graphene layer in the exposed core of the optical fiber by pressing the metallic graphene layer transferred on the stamper in the exposed core of the optical fiber.

12. The preparing method of claim 11, further comprising:
    coating the metallic graphene layer in the exposed core of the optical fiber by pressing the metallic graphene layer transferred on the stamper in a circumferential direction of the exposed core of the optical fiber.

13. The preparing method of claim 9, wherein the process of forming the metallic graphene layer in the exposed core of the optical fiber includes:
    forming the metallic graphene layer in the exposed core of the optical fiber by spraying method.

14. The preparing method of claim 9, further comprising:
    treating a surface of the exposed core area of the optical fiber with UV or plasma before forming the metallic graphene layer in the exposed core of the optical fiber.

15. The preparing method of claim 9, wherein the metallic graphene layer is formed to have a controlled area and thickness by a chemical vapor deposition method.

16. The preparing method of claim 9, further comprising:
    forming a multi-layered metallic graphene layer by repeating the process of forming the metallic graphene layer in the exposed core of the optical fiber.

17. The preparing method of claim 9, wherein the forming of the metallic graphene layer involves forming the metallic graphene layer on a depression formed in the core by removing the portion of the core.

18. The preparing method of claim 9, wherein a ring structure of the metallic graphene layer is formed substantially parallel to the metallic graphene layer formed in the core, wherein the ring structure is a 5-membered, 6-membered, or 7-membered ring structure.

19. A surface plasmon resonance sensor system comprising:
- a surface plasmon resonance sensor including a metallic graphene layer formed in a core of a predetermined area of an optical fiber from which a jacket, and a cladding and a portion of the core are removed;
- a light source unit that supplies an incident light to the metallic graphene layer; and
- a light receiving unit that senses a reflection light reflected by the metallic graphene layer among the incident light
- wherein the metallic graphene layer is a planar monolayer sheet of graphene or a plurality of planar monolayer sheets of graphene stacked together.

20. The surface plasmon resonance sensor system of claim 19, wherein the surface plasmon resonance sensor system senses a chemical material or a bio material.

21. The surface plasmon resonance sensor system of claim 19, wherein the metallic graphene layer is single-layered or multi-layered.

22. The surface plasmon resonance sensor system of claim 19, wherein the core of the optical fiber includes at least one selected from a group consisting of an inorganic material, an organic material and a combination thereof.

23. The surface plasmon resonance sensor system of claim 19, wherein the optical fiber includes a multimode optical fiber.

24. The surface plasmon resonance sensor system of claim 19, wherein the core of the predetermined area of the optical fiber on which the metallic graphene layer is formed has a planar or curved surface shape.

* * * * *